(12) United States Patent
Chatterjee et al.

(10) Patent No.: US 11,361,669 B2
(45) Date of Patent: Jun. 14, 2022

(54) METHOD AND SYSTEM FOR ASSESSING LEARNING EXPERIENCE OF A PERSON

(71) Applicant: Tata Consultancy Services Limited, Mumbai (IN)

(72) Inventors: Debatri Chatterjee, Kolkata (IN); Aniruddha Sinha, Kolkata (IN); Rahul Dasharath Gavas, Kolkata (IN); Rajat Kumar Das, Kolkata (IN); Arijit Sinharay, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 977 days.

(21) Appl. No.: 15/286,127

(22) Filed: Oct. 5, 2016

(65) Prior Publication Data

US 2017/0103668 A1  Apr. 13, 2017

(30) Foreign Application Priority Data

Oct. 7, 2015  (IN) .......................... 3813/MUM/2015

(51) Int. Cl.
*G09B 7/12* (2006.01)
*G16H 10/20* (2018.01)
(Continued)

(52) U.S. Cl.
CPC .............. *G09B 7/12* (2013.01); *A61B 5/0205* (2013.01); *A61B 5/02405* (2013.01); *A61B 5/0533* (2013.01); *A61B 5/14551* (2013.01); *A61B 5/165* (2013.01); *A61B 5/168* (2013.01); *A61B 5/316* (2021.01); *A61B 5/369* (2021.01); *A61B 5/4884* (2013.01); *A61M 21/00* (2013.01); *A63F 13/212* (2014.09); *G16H 10/20* (2018.01); *G16H 20/70* (2018.01); *A61B 5/02416* (2013.01);
(Continued)

(58) Field of Classification Search
None
See application file for complete search history.

(56) References Cited

U.S. PATENT DOCUMENTS

2014/0347265 A1   11/2014   Aimone et al.

FOREIGN PATENT DOCUMENTS

WO   WO 2014/040175 A1   3/2014
WO   WO 2015/027079 A1   2/2015

OTHER PUBLICATIONS

Berta et al., "Electroencephalogram and Physiological Signal Analysis for Assessing Flow in Games", Journal, IEEE Transactions on Computational Intelligence and AI in Games, vol. 5, issue 2, 1 coversheet and pp. 1-12, 2013.

*Primary Examiner* — James B Hull
(74) *Attorney, Agent, or Firm* — Finnegan, Henderson, Farabow, Garrett & Dunner, LLP

(57) ABSTRACT

A method and system is provided for assessing the learning experience of the person by monitoring the mental state of the person. The method involves measuring the brain signal, skin conductance using GSR device, and heart rate variability using the pulse oximeter. These physiological signals are measured when the person is performing an activity such as the modified Stroop test. Once the activity is performed, an offline questionnaire is also filled by the person. Based on the comparison of the offline questionnaire and the physiological signals, a model is generated. This model is used to assess the learning experience of the person. According to another embodiment, a method is also provided for maintaining the steady flow state of a person while performing any activity.

14 Claims, 6 Drawing Sheets

(51) Int. Cl.
*A61B 5/024* (2006.01)
*A61B 5/0533* (2021.01)
*A61M 21/00* (2006.01)
*A61B 5/00* (2006.01)
*A61B 5/16* (2006.01)
*G16H 20/70* (2018.01)
*A61B 5/316* (2021.01)
*A61B 5/369* (2021.01)
*A63F 13/212* (2014.01)
*A61B 5/0205* (2006.01)
*A61B 5/1455* (2006.01)

(52) U.S. Cl.
CPC ... *A61M 2021/005* (2013.01); *A61M 2230/06* (2013.01); *A61M 2230/10* (2013.01); *A61M 2230/205* (2013.01); *A61M 2230/65* (2013.01)

METHOD AND SYSTEM FOR ASSESSING LEARNING EXPERIENCE OF A PERSON

CROSS-REFERENCE TO RELATED APPLICATIONS AND PRIORITY

The present application claims priority from Indian provisional specification no. 3813/MUM/2015 filed on 7 Oct. 2015, the complete disclosure of which, in its entirety is herein incorporated by references.

TECHNICAL FIELD

The present application generally relates to assessment of mental state of a person. More particularly, but not specifically, the invention provides a method and system for assessing the learning experience of the person by assessing the mental state of the person.

BACKGROUND

Teaching professionals have observed that children have limitless curiosity for knowledge before they enter school. Several years later, those same children lack attention, motivation and suffer from boredom. Finally, they disengage themselves from learning and have a negative feeling towards knowledge and learning. This is true for working professionals as well as they need to go through various training programs for new knowledge/skill development. The main purpose of any work or activity is to assess the learning experience by measuring person's engagement as well as enjoyment with the help of positive psychology.

In psychology, cognitive flow is a state of mind involving complete attention with a sense of enjoyment. A person's skill and the challenge of a task together result in different emotional states. When skill is too low and the task too challenging, people become anxious. Alternatively, if the task is too easy and skill is comparatively higher, people become bored. However, when the skill and the challenge are relatively proportional, people enter in a flow state, i.e. state of focused concentration and enjoyment.

It is very challenging to provide a learning experience to a person in which a steady flow state is maintained i.e. which is meaningful, motivated and at the same time enjoyable in nature. This often affects the students who cannot learn or do not want to learn due to lack of engagement or guidance. The same is also true for the working professional in industries. It is very necessary to provide steady flow state to a learner.

There are different approaches for measuring the flow state mainly indirect and direct approach. Indirect approach involves namely, (i) semi-structured interviews—for measuring a qualitative performance, (ii) questionnaires—flow state questionnaires/scales used to describe user experience and performance, (iii) experience sampling method—objective is to measure flow and other states of consciousness occurring in activities encountered in everyday life. Another method had been devised, which involves a feedback-questionnaire based method to evaluate flow, popularly known as the flow state-scale. These feedback or indirect questionnaire based approaches seem to be feasible and less complex, but they are not reliable enough.

The direct approaches involve analyzing the brain signals captured using techniques like functional Magnetic Resonance Imaging (fMRI), functional Near Infra-Red (fNIR) etc. Currently, Electroencephalography (EEG) is extensively being used in educational tasks through the advent of Brain Computer Interface (BCI) technology. In a research, greater left temporal alpha activity was noticed when compared to that of right temporal lobe affecting the performance associated with flow. In conjunction to this, the mid beta activity and theta activity also have an effect on performance whereas there was no significant results with respect to delta waveforms. In higher alpha activity coupled with lower beta activity is found to be characterized for flow state.

Prior attempts at such EEG measurements, however, have not been fruitful because of two major shortcomings. First, there was the failure to measure brain activity while the subject performed a task taxing the subject's mental processes, such as working memory, that are highly related to overall performance. Merely recording brain activity while the subject sits idly, watching a meaningless flashing light, or performing a task not requiring her or his full attention is insufficient to produce patterns of brain activity characterizing changes in an individual's overall performance over an extended time period. Second, there was a reliance on single, overly simplistic measures of brain function derived from theoretical constructs without sufficient support from empirical data.

There is currently no method that quickly and objectively measures an individual's overall performance. Moreover, there is no work that provides a formal way of measuring the performance of a subject in terms of boredom-flow models for web based learning. Though various other methods have been used in this field of the technology, hut none of them focuses on personalized learning of the individual.

SUMMARY

Embodiments of the present disclosure present technological improvements as solutions to one or more of the above-mentioned technical problems recognized by the inventors in conventional systems.

The present application provides a processor implemented method for assessing the learning experience of a person. Initially a task is performed by the person for a predefined time period. The task is performed using a keyboard. At the same time a pattern of a plurality of keys pressed on the keyboard are recorded during the predefined time period while the person performing the task. Simultaneously, the brain activity of the person is measured by sensing an electroencephalogram (EEG) signal using an EEG device during the predefined time period. The concentration of the person is measured by sensing galvanic skin response (GSR) using a GSR sensing device during the predefined time period. The stress level of the person is measured by sensing heart rate variability (HRV) during the predefined time period. Once the task is over, the psychological experience of the person is also acquired using a questionnaire filled by the person. In the next step, the EEG signal, the GSR and the HRV is compared to the results of the questionnaire and the pattern of the plurality of keys pressed by a processor. And finally a model is generated by the processor based on the comparison. The model is configured to be used to assess the learning experience of the person.

According to another embodiment a system is also provided for assessing the learning experience of the person. The system comprises a console, a keyboard in connection with the console, an electroencephalogram (EEG) device, a GSR sensing device, pulse oximeter, a questionnaire and a processor. The console is used by the person to perform a task. The keyboard is used by the person by pressing a plurality of keys in response to the task. The EEG device measures brain activity of the person. The brain activity indicates a skill-challenge balance of the person. The GSR sensing device measures galvanic skin response (GSR) of the person. The GSR indicates the concentration of the person. The pulse oximeter for sensing photo-plethysmogram (PPG) signal, the PPG signal is being used to measure heart rate variability (HRV) of the person, wherein the HRV indicates the stress level of the person. The questionnaire is filled by the person after completing the task, to have an indication of their perception of flow and boredom. The processor configured to compare the EEG signal, the GSR and the HRV to the results of the questionnaire and a pattern of the plurality of keys pressed on the keyboard, the processor further configured to generate a model based on the comparison, wherein the model is configured to be used to assess the learning experience of the person.

In another embodiment, a non-transitory computer-readable medium having embodied thereon a computer program for assessing the learning experience of a person. Initially a task is performed by the person for a predefined time period. The task is performed using a keyboard. At the same time a pattern of a plurality of keys pressed on the keyboard are recorded during the predefined time period while the person performing the task. Simultaneously, the brain activity of the person is measured by sensing an electroencephalogram (EEG) signal using an EEG device during the predefined time period. The concentration of the person is measured by sensing galvanic skin response (GSR) using a GSR sensing device during the predefined time period. The stress level of the person is measured by sensing heart rate variability (HRV) during the predefined time period. Once the task is over, the psychological experience of the person is also acquired using a questionnaire filled by the person. In the next step, the EEG signal, the GSR and the HRV is compared to the results of the questionnaire and the pattern of the plurality of keys pressed by a processor. And finally a model is generated by the processor based on the comparison. The model is configured to be used to assess the learning experience of the person.

It is to be understood that both the foregoing general description and the following detailed description are exemplary and explanatory only and are not restrictive of the invention, as claimed.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and system disclosed. In the drawings.

Figure 1:
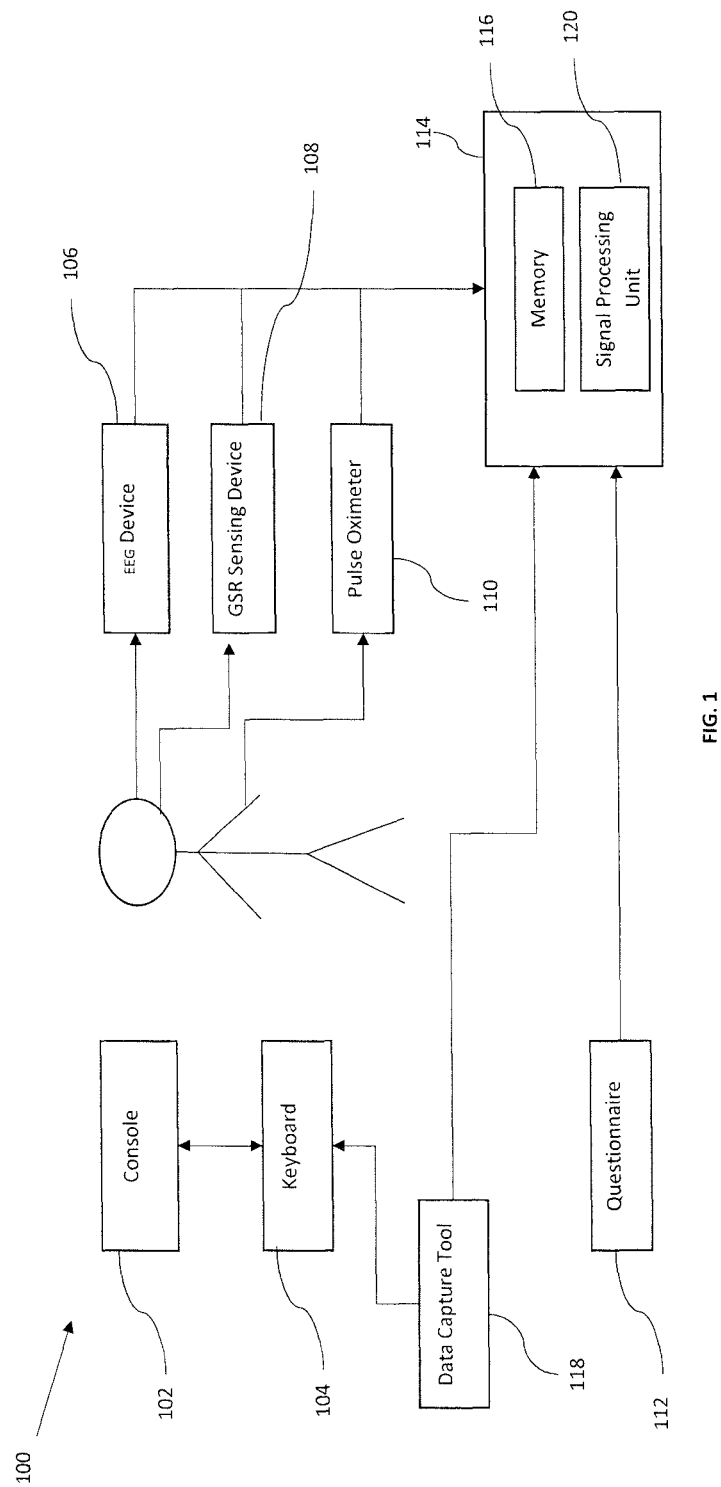
FIG. 1 shows a block diagram of a system for assessing the learning experience of a person in accordance with an embodiment of the invention.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE INVENTION

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. In the following description for the purpose of explanation and understanding reference has been made to numerous embodiments for which the intent is not to limit the scope of the invention.

One or more components of the invention are described as module for the understanding of the specification. For example, a module may include self-contained component in a hardware circuit comprising of logical gate, semiconductor device, integrated circuits or any other discrete component. The module may also be a part of any software programme executed by any hardware entity for example processor. The implementation of module as a software programme may include a set of logical instructions to be executed by a processor or any other hardware entity.

The disclosed embodiments are merely exemplary of the invention, which may be embodied in various forms.

The elements illustrated in the Figures interoperate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as being stored in memories, all or part of the systems and methods consistent with the attrition warning system and method may be stored on, distributed across, or read from other machine-readable media.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk.

The present application provides a method for assessing the learning experience of a person. Initially a task is performed by the person for a predefined time period. The task is performed using a keyboard. At the same time a pattern of a plurality of keys pressed on the keyboard are recorded during the predefined time period while the person performing the task. Simultaneously, the brain activity of the person is measured by sensing an electroencephalogram (EEG) signal using an EEG device during the predefined time period. The concentration level of the person is measured by sensing galvanic skin response (GSR) using a GSR sensing device during the predefined time period. The stress level of the person is measured by sensing heart rate variability (HRV) during the predefined time period. Once the task is over, the psychological experience of the person is also acquired using a questionnaire filled by the person. In the next step, the EEG signal, the GSR and the HRV is compared to the results of the questionnaire and the pattern of the plurality of keys pressed by a processor. And finally a model is generated by the processor based on the comparison. The model is configured to be used to assess the learning experience of the person.

Figure 2:
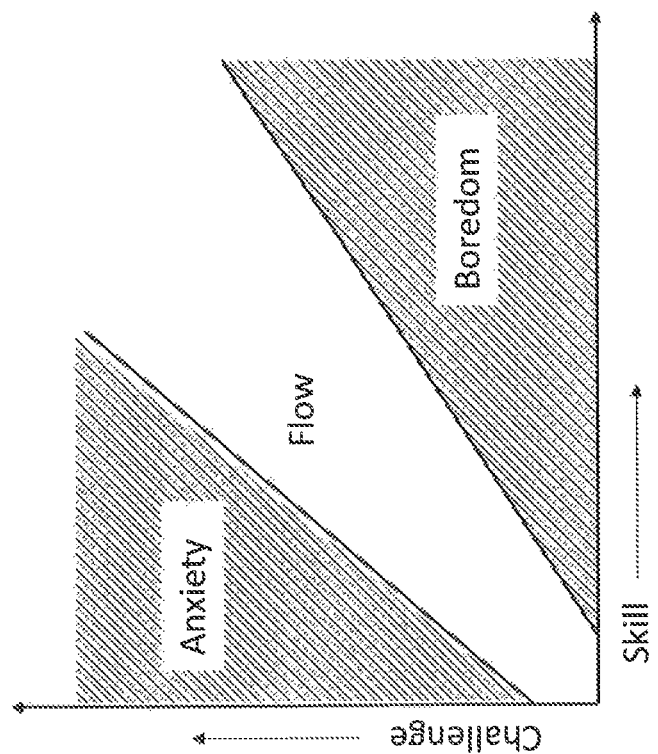
FIG. 2 shows a graphical representation of the flow state, anxiety and boredom state in accordance with an embodiment of the invention.

FIG. 1 illustrates a schematic block diagram of a system 100 for assessing the learning experience of a person according to an illustrative embodiment of the present invention. The learning experience of person is assessed by measuring the flow state of the person. The flow state of the person is directly associated with the mental state of the person. The flow state can determine whether the person is in anxiety state or boredom state as shown in the graph 400 of FIG. 2. When skill is too low and the task too challenging, the person becomes anxious. Alternatively, if the task is too easy and skill is comparatively higher, the person becomes bored. However, when skill and challenge are roughly proportional, people enter flow state i.e. a state of focused concentration and enjoyment.

The system 100 includes a console 102, a keyboard 104 in connection with the console 102, an electroencephalogram (EEG) device 106, a galvanic skin response (CM) sensing device 108, a pulse oximeter 110, a questionnaire 112, and a processor 114. The processor 114 further includes a memory 116, which is configured to store the data generated by various components of the system 100. The system 100 also includes a signal processing unit 120 to pre-process the EEG signal captured by the BEG device 106.

According to an embodiment, the person is asked to perform an activity or a task. The task is performed by the person using the console 102. A game is used as the task which is performed by the person. The game is a modified version of the Stroop test and the standard Tetris game. In an example of the invention, the game is developed using Pygame. The names of the colors used in the Stroop test descend from the top of the screen. The playing field is 24 cells high and 14 cells wide. The task is designed into two versions to induce flow and boredom conditions with variations in speed of the falling words. Seven different colored containers are placed at the bottom of the screen with a fixed distance between each of them. The person is supposed to drop the falling texts into the appropriate containers so that the font color of the failing text matches with the color of the container. The subjects have the provisions to control only the left and the right movements of the falling texts and not the down movement. These movements are implemented using left and right arrow keys of the standard QWERTY keyboard.

Figure 3:
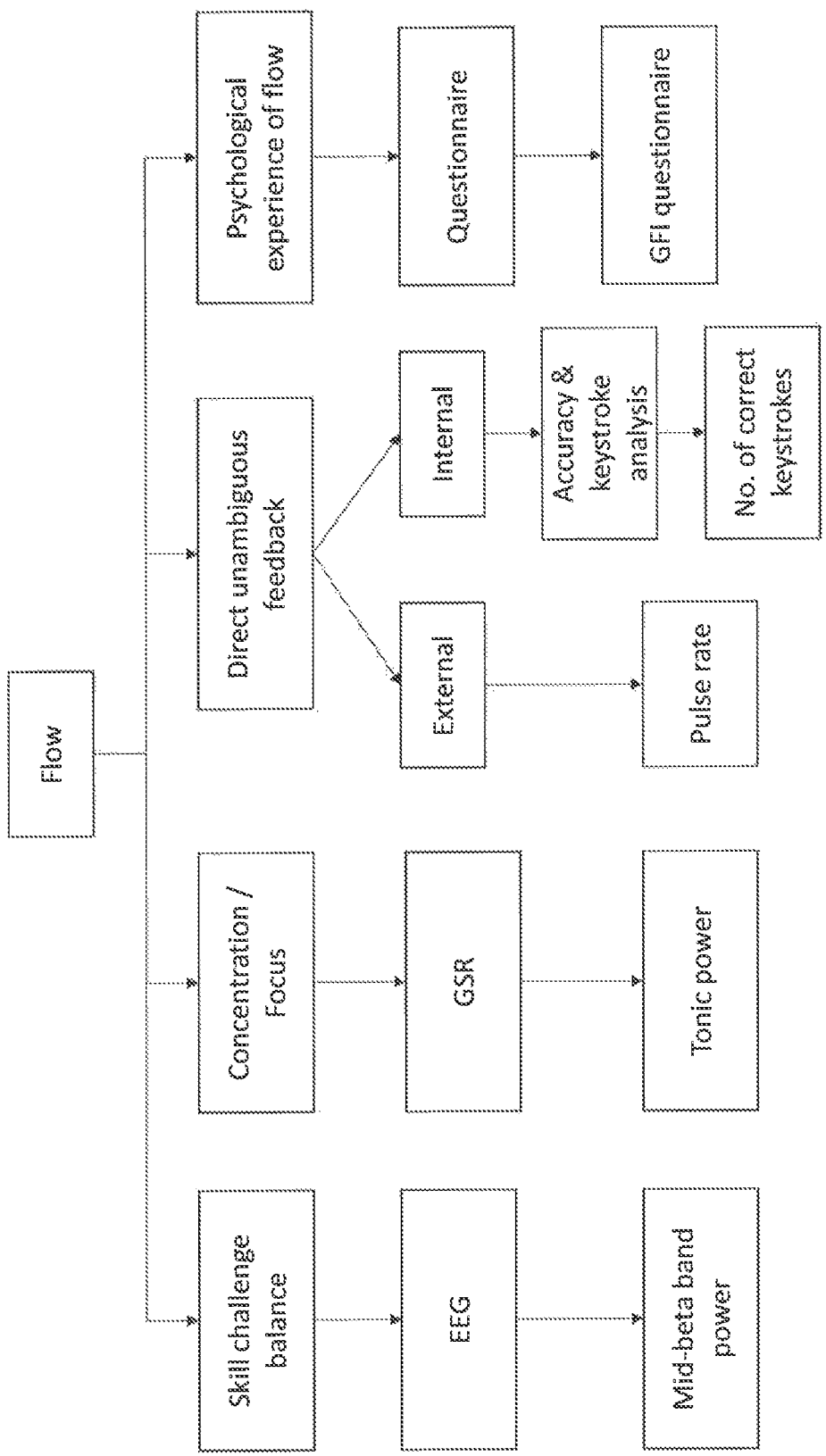
FIG. 3 shows a schematic representation of the dimensions of flow experience and corresponding measurement approaches in accordance with an embodiment of the invention.

The task is always performed for a predefined time period. During the predefined time period when the task is performed, various experience of the flow state are also measured. A schematic representation of the dimensions of flow experience and corresponding measurement approaches is shown in FIG. 3. According to flow theory, there are basically nine dimensions which are indicative of flow experience, namely, skill-challenge balance, concentration and focusing, direct and unambiguous feedback, loss of self-consciousness, clear goals, and sense of control, time transformation, autotelic experience, and action awareness merging. Out of these nine dimensions, three are measured using direct measurement approach and remaining are measured using questionnaire. The three direct measurement approach involves the measurement of EEG, GSR and direct ambiguous feedback through HRV and keystroke analysis.

According to an embodiment of the invention, the skill-challenge balance is measured by sensing the direct electrical activities from the brain using the EEG device 106. In an example of the invention, Neurosky EEG device has been used to capture the electrical activities of the brain. The person is asked to play the game while wearing a single lead EEG device from Neurosky, it is a dry sensor with a lead placed in FP1 position and the grounding is done with reference to left earlobe. The EEG signals along with certain metadata are recorded using an in-house Python based setup at a sampling rate of 512 Hz. The metadata includes the time stamps related to the presentation of various texts (Stroop color) on the screen along with the state of the game. The state of the game is related to the speed in which the texts move. For the purpose of analysis, mid-beta and theta frequency of the EEG signal are important.

According to an embodiment of the invention, the concentration and focus of the person is measured using the galvanic skin response of the person using the galvanic skin response (GSM sensing device 108. The GSR is an electrodermal response where the skin conductance changes with the state of the sweat glands in presence of stressful, likeable events. Therefore GSR is be a good predictor of concentration, mental workload etc. in flow study. The GSR device 108 applies a constant voltage to the skin of the person through two electrodes. The voltage is so small that it cannot be felt or perceived by the individual. However, the current that flows through the skin, as the voltage is applied, can be detected. The GSR signal is characterized by two components: a fast component called 'phasic' and a slow component called 'tonic'. Both tonic and phasic components contain information associated with specific physiological aspects of brain states. Here the tonic component is calculated only by taking the inverse transform of first few Fourier coefficients as given in equation 1, whereas the phasic component is calculated by inversing the higher coefficient of Fourier coefficients as given in equation 2.

$$\text{tonic component} = IFFT\left(\sum_{n=0}^{N-1} x(n) \cdot e^{-j\left(\frac{2\pi}{N}\right)nk}\right), k = 0, 1, 2, 3 \qquad 1$$

$$\text{phasic component} = IFFT\left(\sum_{n=0}^{N-1} x(n) \cdot e^{-j\left(\frac{2\pi}{N}\right)nk}\right), \quad (2)$$

$$k = 4, 5, \ldots N - 1$$

According to an embodiment of the invention, the direct unambiguous feedback of the person is measured to check how well the activity is being performed. There are two ways of evaluating the performance of the person, through internal feedback and external feedback. The internal feedback is provided by the bodily movements. The external feedback is provided by the external feedback is provided by the sources outside the body.

According to an embodiment of the invention, the internal feedback is assessed by monitoring the stress. The stress can be measured using the heart rate variability (HRV) of the person. When the challenge of the undertaking activity is low compared to the person's skill level, then the heart rate variability (HRV) is high compared to the flow state where the skill matches with the challenge level required. The HRV of the person can be measured using the pulse oximeter 110 wearable on the index finder for sensing the Photoplethysmogram (PPG) signal. In an embodiment of the invention, the HRV is calculated in three time domain HRV parameters namely 1) rMSSD (Root mean square of successive differences between adjacent NN intervals), 2) SDSD (Standard deviation of successive differences between adjacent NN intervals), 3) SDNN (Successive difference between NN Intervals).

According to an embodiment of the invention, the external feedback is provided using the keystroke analysis and overall score of the game. A data capture tool 118 was designed to log all the keystrokes (both left keystroke and right keystrokes) while playing the game (the task). The score was initially set to zero and was incremented by one, each time the user successfully placed the falling texts in the corresponding containers. At the end of the game timer, the total score is displayed on the screen. For each falling text, total number of left keystrokes $N_{KL}$ and total number of right keystrokes $N_{KR}$ were extracted from the data file generated by the data capture tool 118. For each text to be collected in the correct container, the person needs to press either left key or the right key. Hence majority key-presses actually represents the correct number of keystrokes for that particular object. If $N_{KL} \gg N_{KR}$ then number of correct keys $N_{KC}$ is given by equation 3. Similarly if $N_{KL} \ll N_{KR}$ then the number of correct keys is given by equation 4. The total number of keystrokes for a particular falling text is given by equation 5.

$$N_{KC} = N_{KL} - N_{KR} \quad (3)$$

$$N_{KC} = N_{KR} = N_{KL} \quad (4)$$

$$N_K = N_{KL} + N_{KR} \quad (5)$$

Then, the keystroke precision measure is calculated by dividing the total number of correct keystrokes by total keystrokes using equation 6.

$$C = (N_{KC}/N_K) \quad (6)$$

For boredom condition C is close to 1 as all the keystrokes are expected to be the correct ones. As the speed of the falling object increases, subjects tend to press some wrong keys and the value of correctness measure decreases. In the anxiety condition, the number of wrong keystroke is expected to be maximum and hence value of C is minimum.

According to an embodiment of the invention, the, remaining six dimensions of the flow are evaluated by a questionnaire based survey as they are mainly related to human perception. After finishing the game, the users are asked to fill up a questionnaire to obtain an indication of their perception during flow and boredom experience. For this purpose a 7 point rating scale called Game Flow Inventory (GFI) has been generated, GFI has been derived from original 13 point flow rating scale and is specifically applicable for gaming environments. GFI measures level of engagement, enjoyment or happiness and intrinsic motivation.

The data generated by the EEG device 106, the GSR sensing device 108, the pulse oximeter 110, the keystroke analysis and the questionnaire 112 is configured to be used to generate a model which can be used to assess the learning experience of the person. The data generated by the EEG device 106, the GSR sensing device 108, the pulse oximeter 110, the keystroke analysis and the questionnaire 112 is given to the processor 114. The processor 114 is configured to compare the EEG signal, the GSR and the HRV to the results of the questionnaire and the output of the keystroke analysis to generate the model based on the comparison.

The model is used to assess the learning experience of the person. According to an embodiment of the invention, the person is shown two types of learning materials from web where one is in the interest area of the subject and other is in an unrelated area. The goal is to derive certain attributes for the subject for a given learning material. This is done using different types of sensing. Using the EEG analysis, the state transition probabilities ($P_{ij}^i$ where i,j∈{bo, fl}) for the learning session are derived using a two state Markov chain whose states were earlier modeled with the help of the modified Tetris game. A distance metric $D^k$, k∈{bo, fl} is computed to analyze the closeness of the Markov chain for the learning material with the previously generated boredom and flow Markov chains using the modified Tetris game. The distance metric $D^k$ gives an estimate on the overall experience of the person related to boredom and flow. As per equation 7 and 8.

$$D^{bo} = \text{abs}\left(\sum_{i \in (bo,fl)} \sum_{j \in (bo,fl), j \neq i} \left(p_{ij}^{g,bo} - p_{ij}^t\right)\right) \quad (7)$$

$$D^{fl} = \text{abs}\left(\sum_{i \in (bo,fl)} \sum_{j \in (bo,fl), j \neq i} \left(p_{ij}^{g,fl} - p_{ij}^t\right)\right) \quad (8)$$

Figure 4:
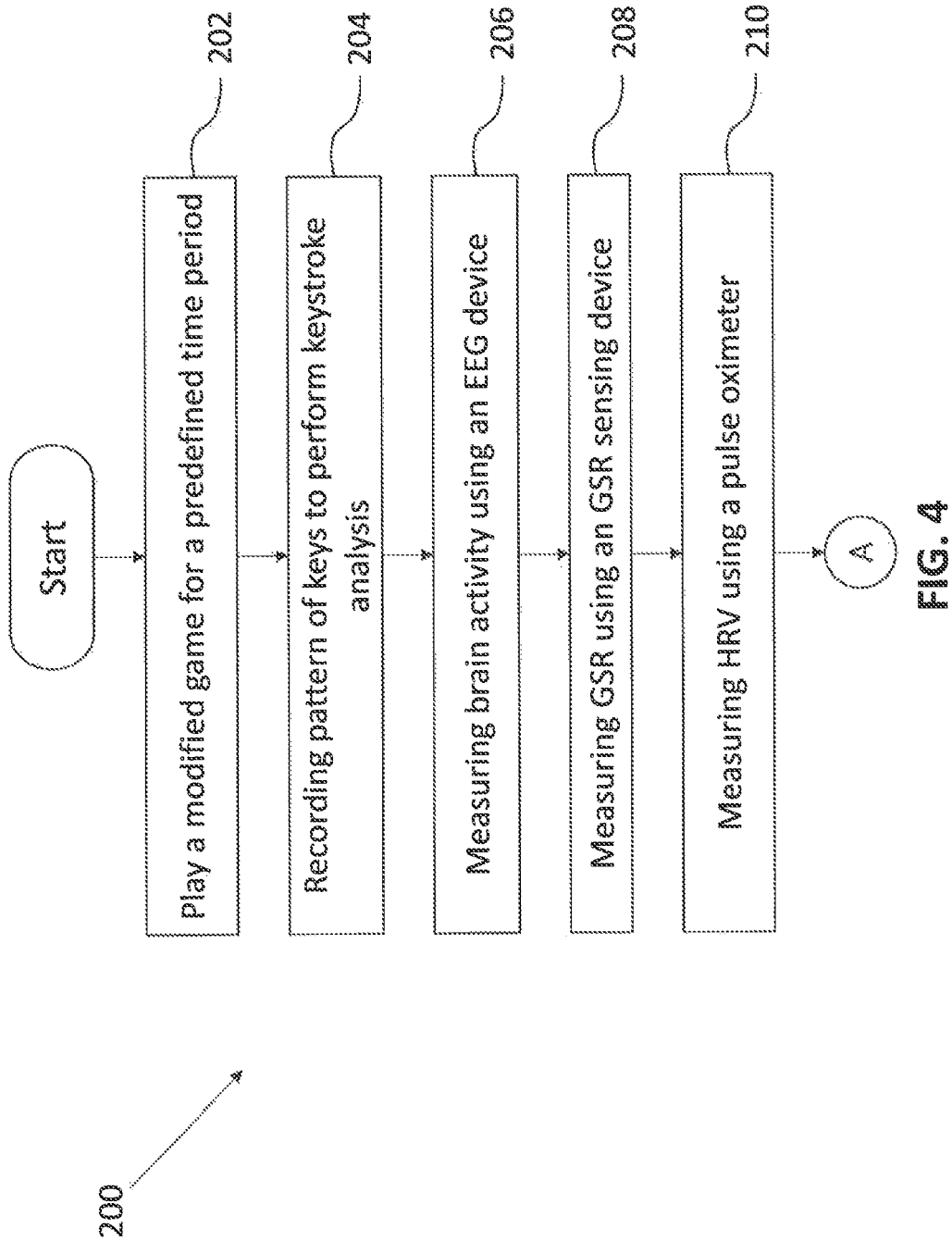
FIG. 4 shows a flow chart illustrating steps involved in assessing the learning experience of the person in accordance with an embodiment of the invention.
Figure 4:
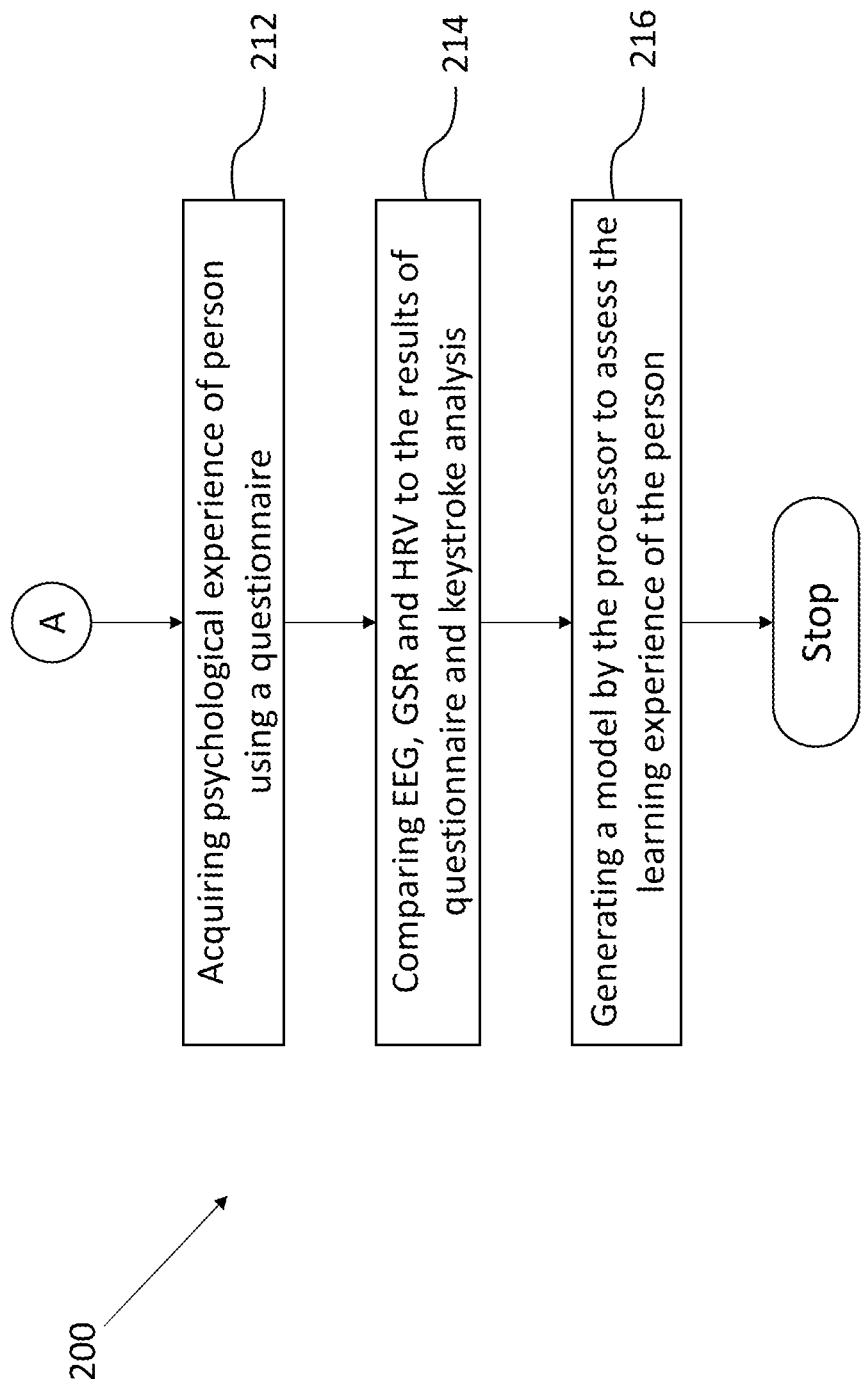

A flowchart 200 illustrating the steps involved in assessment of the learning experience of the person is shown in FIG. 4 according to an illustrative embodiment of the invention. At step 202, the person is asked to perform a task for a predefined time period. Normally, a modified game is asked to be played by the person. The game is a modified version of the Stroop test and the standard Tetris game. At the next step 204, simultaneously when the person is performing that the task, the recording pattern of the plurality of key present on the key board is also recorded by the data capture tool 118. At step 206, the electrical signal generated by the brain is measured using the EEG device 106. EEG signal measures the skill-challenge balance of the person. In an example, a standard Neurosky device has been used for the measuring. The EEG device 106 captures mid-beta and theta frequency of the EEG signal for the analysis. In the next step 208, the galvanic skin response (GSR) is measured using the GSR sensing device 108. GSR measures the concentration and focus of the person. In the next step 210, heart rate variability (HRV) of the person is measured using the pulse oximeter 110. HRV is the indicator of the stress faced by the person while playing the game. It should be appreciated that the step 206, 208 and 210 are being performed simultaneously when the person is performing the activity. At the next step 212, psychological experience of the person is acquired using the questionnaire 112. The person is asked to fill up the questionnaire after finishing the task. The questionnaire 112 is used to obtain an indication of person's perception during flow and boredom experience. For this purpose a seven point rating scale called Game Flow Inventory (GFI) has been generated.

In the next step 214, the EEG signal, the GSR, and the HRV is compared with the results of the questionnaire and the output of the keystroke analysis by the processor 114. And finally at the last step 216, a model is generated by the processor based on the comparison. The model is then used to assess the learning experience of the person.

Figure 5:
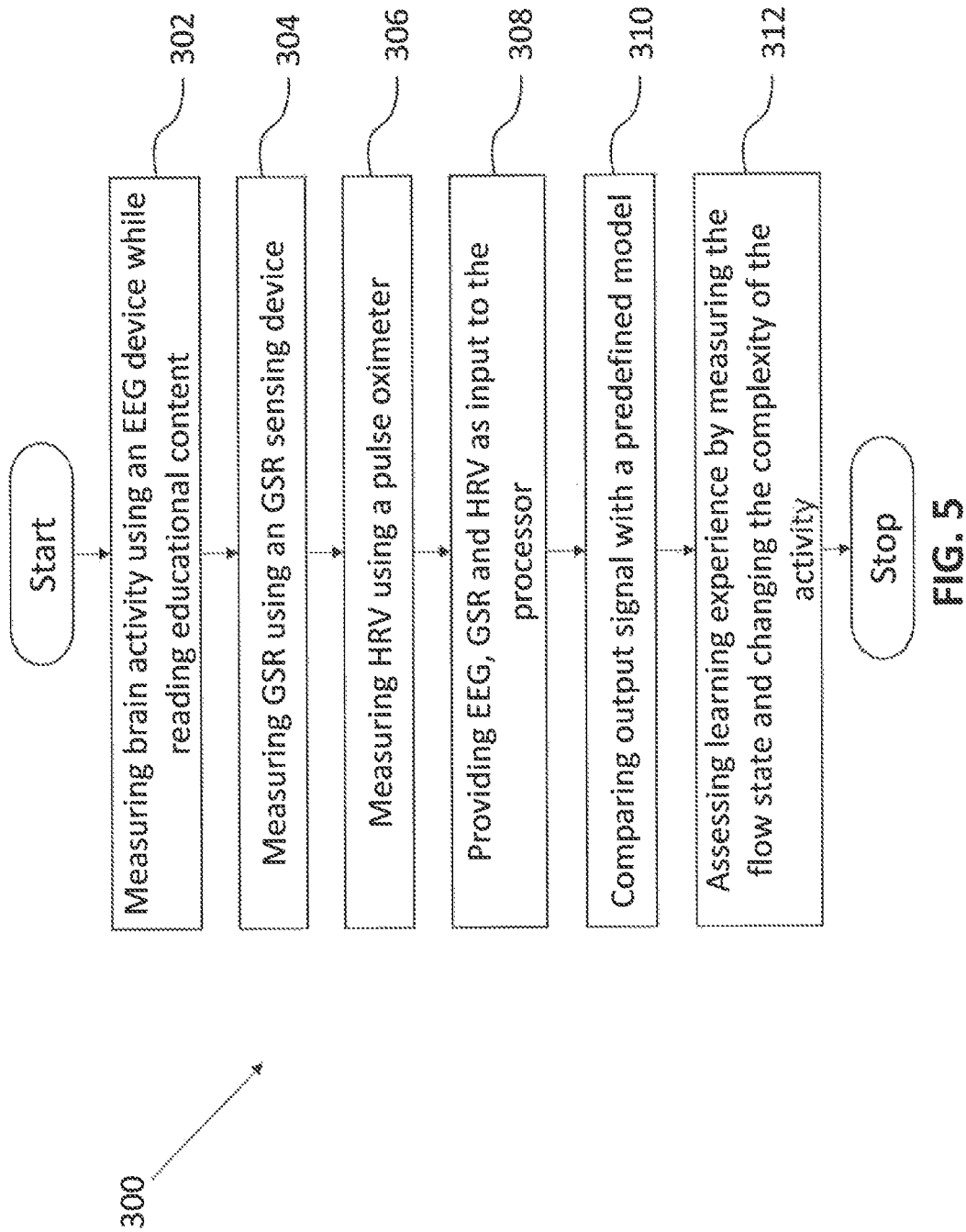
FIG. 5 shows a flow chart illustrating steps involved in maintaining the steady flow state of the person while performing an activity in accordance with another embodiment of the invention.

According to another embodiment of the invention, a flowchart 300 for maintaining the steady flow state of the person during performing an activity is shown in FIG. 5. It should be appreciated that the activity could be a test such as Tetris based game etc. or a practical learning exercise for example, web base learning activity etc. It should be appreciated that the activity can also include reading an educational content. So initially, at step 302, brain activity of the person is measured using the EEG device 106 simultaneously when the person is performing the activity. In the next step 304, GSR of the person is measured using the GSR sensing device 108. At step 306, PPG signal is sensed using the pulse oximeter 110. The PPG signal is then used to measure the heart rate variability of the person. It should be appreciated that the step 302, 304 and 306 are being performed simultaneously when the person is performing the activity. In the next step 308, the brain activity, the GSR and the HRV of the person is provided as an input to the processor 114. Based on the provided input, an output signal is generated. In the next step 310, the processor 114 compares the output signal with a predefined model. Finally, at step 312, depending on the comparison of the output signal and the predefined model, the learning experience is assessed by measuring the flow state of the person, and the complexity of the activity is changed to maintain the steady flow state of the person. It should be appreciated that the predefined model can be generated by following the steps mentioned in the flowchart 200.

A working example of the present invention is explained as follows:

A group of 20 people, 10 male and 10 female were randomly selected to perform the experiments. They were all right handed engineers having normal or corrected to normal 6/6 vision with spectacles. The average age group of the subjects selected was 28-32 years. While selecting the subjects we also ensured that they are from similar cultural and educational background. These factors were taken into account to ensure minimum variance in brain lateralization across the participants.

Each of the people are asked to play the modified Stroop test game as mentioned above. In this game, for boredom experience, the texts descend down at the rate of 1200 milliseconds per block. In case of flow state inducing condition, the texts initially descend at the rate of 1000 milliseconds per cell and then decreases by 200 milliseconds at every 30 seconds per two cells. On each correct match, the score is incremented by one. Both the sessions have been designed to run for 2 minutes each. At the end of the game the final score is displayed on the screen.

The physiological data from the person is then collected using an in-house python based data capture tool. The application enables us to show the stimulus in a standard computer screen and at the same time collect the EEG signals. Subjects are asked to play the game while wearing a single lead EEG device from Neurosky. It is a dry sensor with a lead placed in FP1 position and the grounding is done with reference to left earlobe. For recording the variance in skin conductance level, we use a GSR device from eSense. All our participants are right handed and hence we put the GSR sensors on the middle and ring fingers of the left hand. The right hand is kept completely free so that the user can play the game comfortably. The oxygen saturation level and the pulse rate are assessed by the pulse oximeter from Contec (CMS50DL1), through the left index finger. During the gaming session, keystrokes (both left and right), game scores, GSR data, EEG data and SPO2 data were logged in for further analysis.

The experiment has been conducted in a block, in which the experimental task is performed four times: twice during boredom condition and twice under the flow condition. For half of the subjects the order of the conditions are boredom-flow-boredom-flow and for remaining participants the order is flow-boredom-flow-boredom. Each block lasted for 10 minutes and consisted of two tasks: 1) participants performed the experimental task for first 8 minutes (2 minutes for each conditions and 2 sessions per conditions) 2) next they completed the questionnaire based survey using GFI.

This application then further used in the Web based learning of the person. The experiment with web based learning is performed on a smaller subset of five subjects. These subjects are selected from the 20 subjects participated in the modified Tetris game. The top four subjects are chosen, whose detection accuracy of the boredom and flow state are maximum for the game task. These subjects were shown two types of videos namely one which is of their interest area and the other which is not. Each of these videos are of duration 5 minutes. The sequence of the two types of videos are distributed among five subjects in a balanced manner.

After performing the above activities, the results were obtained. The feedback of the person was taken using the questionnaire. The overall scores for both flow and boredom questionnaires are calculated assuming 1=strongly disagree, 2=disagree, 3=undecided, 4=agree and 5=strongly agree. Next we performed t-test on the scores obtained to find out the differences between two conditions: flow and boredom. Next we observed the differences in mean and variance for both the conditions for each subject. Based on these differences, we finally concluded that 16 out of 20 subjects actually entered in flow state as there is a significant difference between the mean values. For the remaining two subjects there are no differences between the mean values and hence are not expected to be in flow state. Similarly, the keystroke analysis was analyzed using the left and right key strokes captured by the data capture tool 118. The results of EEG signal capture, GSR and HRV were also analyzed to obtain the model in web based learning. Finally, the model is then used for deriving the flow-boredom state transitions for a given learning material and also getting insights on whether they enter flow state during the learning process.

In view of the foregoing, it will be appreciated that the present invention provides a method and system for assessing the learning experience of person by monitoring the mental activity of the person. Still, it should be understood that the foregoing relates only to the exemplary embodiments of the present invention, and that numerous changes may be made thereto without departing from the spirit and scope of the invention as defined by the following claims.

What is claimed is:

1. A method for assessing the learning experience of a person, the method comprising a processor implemented steps of:
   asking the person to perform a task for a predefined time period, wherein the task is performed using a keyboard;
   recording a pattern of a plurality of keys pressed on the keyboard during the predefined time period while performing the task;
   measuring brain activity of the person by sensing an electroencephalogram (EEG) signal using an EEG device during the predefined time period;
   sensing galvanic skin response (GSR) of the person using a GSR sensing device to measure a skin conductance of the person by applying a constant voltage to skin of the person through two electrodes and detecting the current passing through the skin during the predefined time period, wherein the GSR is an electro-dermal response where the skin conductance changes with a state of the sweat glands in presence of stressful, likeable events, and wherein the GSR is characterized by phasic and tonic components that contain information associated with specific physiological aspects of brain states and are calculated by taking inverse transform of Fourier coefficients, wherein the GSR indicates the concentration of the person;
   measuring a heart rate variability (HRV) of the person using a pulse oximeter wearable on the index finger for sensing a photo-plethysmogram (PPG) signal during the predefined time period, wherein the HRV is calculated in three time domain HRV parameters namely Root mean square of successive differences between adjacent NN intervals, Standard deviation of successive differences between adjacent NN intervals, Successive difference between NN Intervals, wherein the HRV indicates a stress level of the person;
   acquiring psychological experience of the person using a questionnaire filled by the person after performing the task to have an indication of their perception of flow and boredom;
   generating by a processor an output comprising the EEG signal depicting brain activity of the person, the GSR characterized by phasic and tonic components that contain information associated with specific physiological aspects of brain states depicting the concentration of the person and the HRV calculated in three time domain HRV parameters namely Root mean square of successive differences between adjacent NN intervals, Standard deviation of successive differences between adjacent NN intervals, Successive difference between NN Intervals depicting the stress level of the person as input; and
   comparing by the processor, the generated output with a predefined model using a two state Markov chain with distance $D^k$, wherein the distance metric Dk gives an estimate on the overall experience of the person related to boredom and flow and is used to assess the learning experience of the person, and wherein the predefined model is configured to be used to assess the learning experience of the person on whether they enter flow state during the learning process, and wherein comparison is performed by deriving state transition probabilities for the learning session.

2. The method of claim 1, wherein the task includes playing a video game on a console.

3. The method of claim 1 further includes analyzing mid-beta and theta frequency of the EEG signal of the person.

4. The method of claim 1, wherein the learning experience is a web-based learning experience.

5. The method of claim 1, wherein the questionnaire includes a set of questions related to flow and boredom states in the task.

6. The method of claim 5, wherein the set of questions uses a seven point rating scale to measure the flow and boredom state of the person.

7. The method of claim 1, wherein the model is a first order Markov chain model.

8. A system for assessing the learning experience of a person, the system comprising:
   a console configured to be used by the person to perform a task;
   a keyboard in connection with the console, the keyboard configured to be used by the person by pressing a plurality of keys in response to the task;
   an electroencephalogram (EEG) device for measuring brain activity of the person, wherein the brain activity indicates a skill-challenge balance of the person;
   a GSR sensing device for sensing galvanic skin response (GSR) of the person to measure a skin conductance of the person by applying a constant voltage to skin of the person through two electrodes and detecting the current passing through the skin, wherein the GSR is an electro-dermal response where the skin conductance level changes with a state of sweat glands in presence of stressful, likeable events, and wherein the GSR is characterized by phasic and tonic components that contain information associated with specific physiological aspects of brain states and are calculated by taking inverse transform of Fourier coefficients, wherein the GSR indicates the concentration of the person;
   a pulse oximeter wearable on the index finger for sensing photo-plethysmogram (PPG) signal, the PPG signal is being used to measure heart rate variability (HRV) of the person, wherein the HRV is calculated in three time domain HRV parameters namely Root mean square of successive differences between adjacent NN intervals, Standard deviation of successive differences between adjacent NN intervals, Successive difference between NN Intervals, wherein the HRV indicates a stress level of the person;
   a questionnaire configured to be filled by the person after completing the task, to have an indication of the person's perception of flow and boredom;
   a processor configured to generate an output comprising he EEG signal depicting brain activity of the person, the GSR characterized by phasic and tonic components that contain information associated with specific physiological aspects of brain states depicting the concentration of the person and the HRV calculated in three time domain HRV parameters namely Root mean square of successive differences between adjacent NN intervals, Standard deviation of successive differences between adjacent NN intervals, Successive difference between NN Intervals depicting the stress level of the person as input; and
   compare, the generated output with a predefined model using a two state Markov chain with distance $D^k$, wherein the distance metric Dk gives an estimate on the overall experience of the person related to boredom and flow and is used to assess the learning experience of the person, and wherein the predefined model is configured to be used to assess the learning experience of the person on whether they enter flow state during the learning process, and wherein comparison is performed by deriving state transition probabilities for the learning session.

9. The system of claim 8, wherein the console is a video game console.

10. The system of claim 8, wherein the questionnaire is related to the person's perception of flow and boredom experience while performing the task.

11. The system of claim 8, wherein the questionnaire uses a seven point rating scale to measure the flow and boredom state of the person.

12. A non-transitory computer-readable medium having embodied thereon a computer program for assessing the learning experience of a person, a method comprising:
asking the person to perform a task for a predefined time period, wherein the task is performed using a keyboard;
recording a pattern of a plurality of keys pressed on the keyboard during the predefined time period while performing the task;
measuring brain activity of the person by sensing an electroencephalogram (EEG) signal using an EEG device during the predefined time period;
sensing galvanic skin response (GSR) of the person using a GSR sensing device to measure a skin conductance of the person by applying a constant voltage to skin of the person through two electrodes and detecting the current passing through the skin during the predefined time period, wherein the GSR is an electro-dermal response where the skin conductance changes with a state of sweat glands in presence of stressful, likeable events, and wherein the GSR is characterized by phasic and tonic components that contain information associated with specific physiological aspects of brain states and are calculated by taking inverse transform of Fourier coefficients, wherein the GSR indicates the concentration of the person;
measuring heart rate variability (HRV) of the person, using a pulse oximeter wearable on the index finger for sensing a photo-plethysmogram (PPG) signal during the predefined time period, wherein the HRV is calculated in three time domain HRV parameters namely Root mean square of successive differences between adjacent NN intervals, Standard deviation of successive differences between adjacent NN intervals, Successive difference between NN Intervals, wherein the HRV indicates a stress level of the person;
acquiring psychological experience of the person using a questionnaire filled by the person after performing the task to have an indication of their perception of flow and boredom;

generating by a processor an output comprising the EEG signal depicting brain activity of the person, the GSR characterized by phasic and tonic components that contain information associated with specific physiological aspects of brain states depicting the concentration of the person and the HRV calculated in three time domain HRV parameters namely Root mean square of successive differences between adjacent NN intervals, Standard deviation of successive differences between adjacent NN intervals, Successive difference between NN Intervals depicting the stress level of the person as input; and
comparing by the processor, the generated output with a predefined model using a two state Markov chain with distance $D^k$, wherein the distance metric Dk gives an estimate on the overall experience of the person related to boredom and flow and is used to assess the learning experience of the person, and wherein the predefined model is configured to be used to assess the learning experience of the person on whether they enter flow state during the learning process, and wherein comparison is performed by deriving state transition probabilities for the learning session.

13. The method of claim 1, wherein the tonic and phasic components of the GSR are calculated using the equations:

$$\text{tonic component} = IFFT\left(\sum_{n=0}^{N-1} x(n), e^{-j\left(\frac{2\pi}{N}\right)nk}\right), k = 0, 1, 2, 3$$

$$\text{phasic component} = IFFT\left(\sum_{n=0}^{N-1} x(n), e^{-j\left(\frac{2\pi}{N}\right)nk}\right), k = 4, 5, \ldots N-1,$$

wherein the phasic component is a fast component and the tonic component is a slow component and contain information associated with specific physiological aspects of brain states.

14. The system of claim 8, wherein the tonic and phasic components of the GSR are calculated using the equations:

$$\text{tonic component} = IFFT\left(\sum_{n=0}^{N-1} x(n), e^{-j\left(\frac{2\pi}{N}\right)nk}\right), k = 0, 1, 2, 3$$

$$\text{phasic component} = IFFT\left(\sum_{n=0}^{N-1} x(n), e^{-j\left(\frac{2\pi}{N}\right)nk}\right), k = 4, 5, \ldots N-1,$$

wherein the phasic component is a fast component and the tonic component is a slow component and contain information associated with specific physiological aspects of brain states.

* * * * *